(12) United States Patent
Kozloski et al.

(10) Patent No.: US 9,447,448 B1
(45) Date of Patent: Sep. 20, 2016

(54) DRONE-BASED MICROBIAL ANALYSIS SYSTEM

(71) Applicant: International Business Machines Corporation, Armonk, NY (US)

(72) Inventors: James R. Kozloski, New Fairfield, CT (US); Timothy M. Lynar, Kew (AU); Clifford A. Pickover, Yorktown Heights, NY (US); John M. Wagner, Carlton (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/744,663

(22) Filed: Jun. 19, 2015

Related U.S. Application Data

(63) Continuation of application No. 14/687,101, filed on Apr. 15, 2015.

(51) Int. Cl.
  *G05D 1/00* (2006.01)
  *C12Q 1/04* (2006.01)
  *B64C 39/02* (2006.01)

(52) U.S. Cl.
  CPC ............ *C12Q 1/04* (2013.01); *B64C 39/024* (2013.01); *B64C 2201/12* (2013.01); *B64C 2201/141* (2013.01)

(58) Field of Classification Search
  CPC ... C12Q 1/04; B64C 39/024; B64C 2201/12; B64C 2201/141
  USPC ............................................................ 701/2
  See application file for complete search history.

(56) References Cited

U.S. PATENT DOCUMENTS

| | | | |
|---|---|---|---|
| 2009/0228355 A1* | 9/2009 | Dawson | A63F 13/12 705/14.73 |
| 2016/0144358 A1* | 5/2016 | Patel | B01L 3/5027 435/287.2 |

OTHER PUBLICATIONS

Kozloski et al., "Drone-Based Microbial Analysis System", U.S. Appl. No. 14/687,101, filed Apr. 15, 2015.
List of IBM Patents or Patent Applications Treated as Related; (Appendix P), Filed Jul. 20, 2015; 2 pages.

* cited by examiner

*Primary Examiner* — Ian Jen
(74) *Attorney, Agent, or Firm* — Cantor Colburn LLP; Vazken Alexanian

(57) ABSTRACT

A drone-based microbial analysis system includes an electronic drone control facility including an electronic storage memory device. The storage memory device stores information including a location of at least one possible contaminated area previously determined to contain at least one positively-tested microbe. At least one drone vehicle is in signal communication with the drone control facility and autonomously navigates to the at least one possible contaminated area to collect a specimen. The drone control facility performs a microbial analysis based on the collected specimen and confirms the at least one possible contaminated area is a positively contaminated area that contains at least one microbe based on the microbial analysis.

8 Claims, 6 Drawing Sheets

DRONE-BASED MICROBIAL ANALYSIS SYSTEM

DOMESTIC PRIORITY

This application is a continuation of U.S. patent application Ser. No. 14/687,101, filed Apr. 15, 2015, the disclosure of which is incorporated by reference herein in its entirety.

BACKGROUND

The present invention relates to microbial contamination prevention, and more particularly, to a microbial analysis and disinfection control system.

Various environments such as agriculture environments and healthcare environments, for example, are plagued by microbes such as, for example, antibiotic resistant bacteria, mold, pathogens, spores, viruses, or other contaminants. Traditionally, human workers were tasked with the responsibility to detect and disinfect contaminated areas. The demands on these workers include constant vigilance to prevent contaminated areas and opportunities for transmission, as well as costly management of host carriers. In addition, the workers themselves can become colonized by these strains of microbes, and can experience health effects or job loss as a result. As workloads increase with cost-cutting measures, workers are faced with the challenge to manage the cognitive load of identifying likely contaminated areas, disinfect positively identified contamination areas, and prevent the future spread of microbes.

SUMMARY

According to at least one embodiment, a drone-based microbial analysis system includes an electronic drone control facility including an electronic storage memory device. The storage memory device stores information including a location of at least one possible contaminated area previously determined to contain at least one positively-tested microbe. At least one drone vehicle is in signal communication with the drone control facility and autonomously navigates to the at least one possible contaminated area to collect a specimen. The drone control facility performs a microbial analysis based on the collected specimen and confirms the at least one possible contaminated area is a positively contaminated area that contains at least one microbe based on the microbial analysis.

According to another embodiment, a method of performing a microbial analysis comprises determining at least one possible contaminated area, and autonomously navigating at least one drone vehicle to the at least one possible contaminated area to collect at least one specimen. The method further includes performing a microbial analysis based on the collected at least one specimen. The method further includes confirming the at least one possible contaminated area is a positively contaminated area that contains at least one microbe based on the microbial analysis.

According to yet another embodiment, an electronic drone control facility determines whether a possible contaminated area tests positive for at least one microbe. The drone control facility comprises an electronic contaminated location database that stores information indicating at least one possible contaminated area previously determined to contain at least one positively-tested microbe. An electronic drone system module is in signal communication with the electronic contaminated location database. The drone system module includes a computer processor and computer readable instructions that when executed by the computer processor commands at least one drone vehicle to collect at least one specimen from the at least one possible contaminated area. The electronic drone control facility further includes an electronic microbial testing unit is in signal communication with the drone system module. The microbial testing unit includes a computer processor and computer readable instructions that when executed by the computer processor performs a microbial analysis based on the at least one specimen collected by the drone.

Additional features are realized through the techniques of the present invention. Other embodiments are described in detail herein and are considered a part of the claimed invention. For a better understanding of the invention with the features, refer to the description and to the drawings.

BRIEF DESCRIPTION OF THE DRAWINGS

The subject matter which is regarded as the invention is particularly pointed out and distinctly claimed in the claims at the conclusion of the specification. The forgoing features are apparent from the following detailed description taken in conjunction with the accompanying drawings in which:

DETAILED DESCRIPTION

Figure 1:
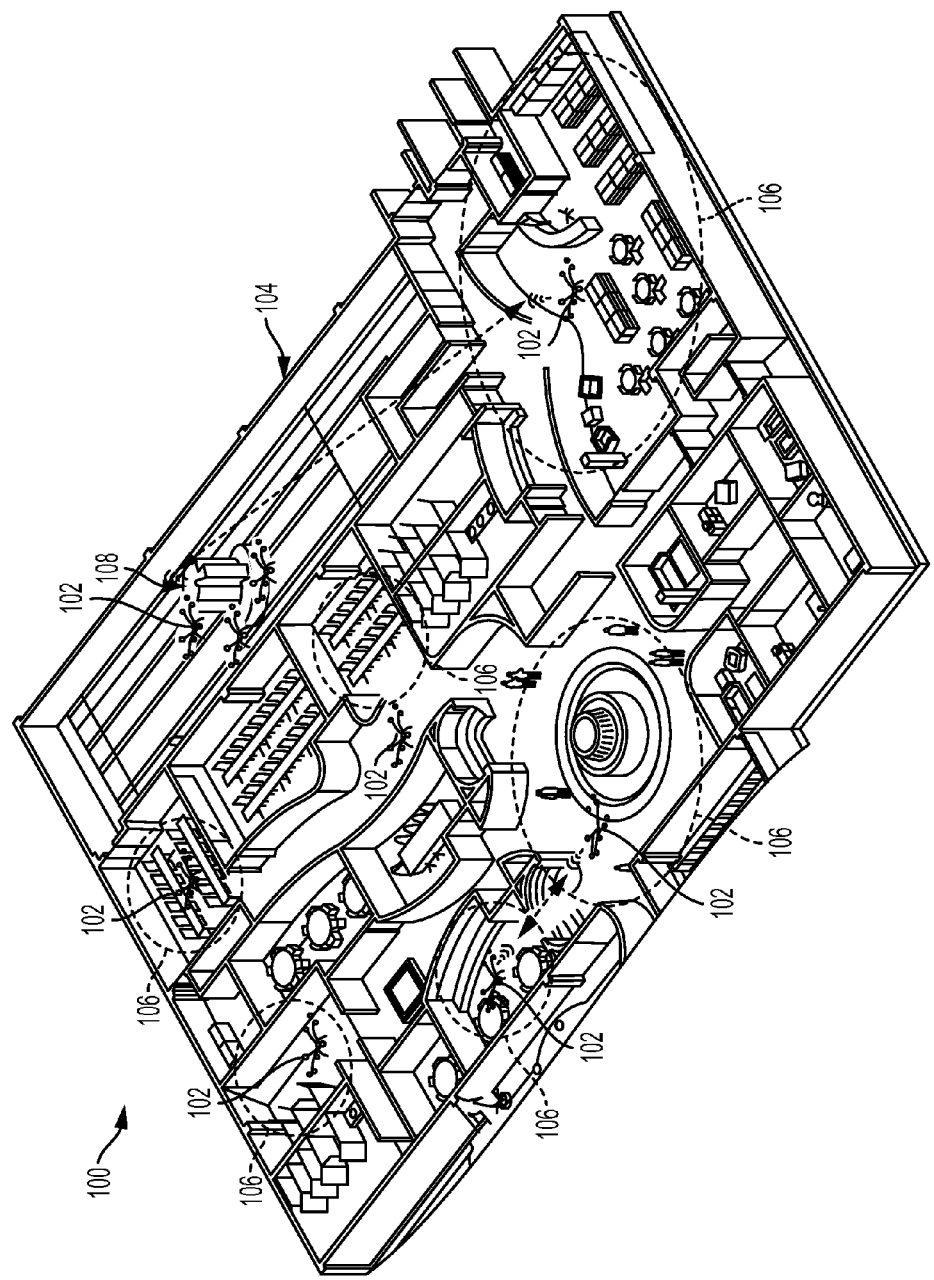
FIG. 1 illustrates a drone-based microbial sampling system that includes a plurality of drone vehicles configured to autonomously navigate about an environment according to a non-limiting embodiment.

With reference now to FIG. 1, a drone-based microbial sampling system 100 is illustrated according to a non-limiting embodiment. The drone-based microbial sampling system 100 is configured to control operation of one or more drone vehicles 102 (i.e., drones 102) that autonomously navigate about an environment 104. The environment includes, but is not limited to, a healthcare facility, an agricultural acreage, an educational facility, a produce facility, etc.

The drones 102 each include a drone microcontroller (not shown in FIG. 1) that performs various flight operations to facilitate the autonomous execution of one or more services/tasks. The autonomous flight operations include, but are not limited to, path planning to determine an optimal path for the drone 102 to navigate about the environment 104 while meeting certain objectives and flight constraints, such as energy requirements, obstacle recognition allowing drones 102 to autonomously avoid obstacles such as walls, humans, buildings, trees, etc. during flight, trajectory generation (i.e., motion planning) to determine optimal control maneuvers in order to follow a path necessary to complete the requested service or task, task regulation to determine specific control strategies required to constrain a vehicle within some tolerance or permissible airspace, task allocation and scheduling to determine the optimal distribution of each service request/task among a plurality of service requests/tasks within time and equipment constraints, and cooperative tactics to formulate an optimal sequence and spatial distribution of activities between agents to maximize the chance of success in any given mission scenario.

The drone-based microbial sampling system 100 further includes a drone control facility 108 that can store or dock each of the drones 102. The drone control facility 108 is also in signal communication with each of the drones 102. In this manner, the drone control facility 108 can establish wireless communication, for example, between each of the drones 102 to wirelessly transmit and receive data. The drone control facility 108 may further include one or more microcontrollers (not shown in FIG. 1), and a data server/memory system (not shown in FIG. 1) configured to electrically store various data and computer-readable instructions. The data may include, but is not limited to, instructions for commanding operation of the drones 102, one or more lookup tables populated with data that identifies each drone 102 registered in the drone-based microbial sampling system 100, one or more maps/blueprints/floorplans of the environment 104, one or more locations of possible contaminated areas 106 within the environment 104, one or more algorithms or sampling tests configured to positively identify microbes included in a sample collected by one or more of the drones 102, and identification information of various known microbes. The drone control facility 108 may further include one or more charging stations and one or more sampling stations as discussed in greater detail below.

Figure 2:
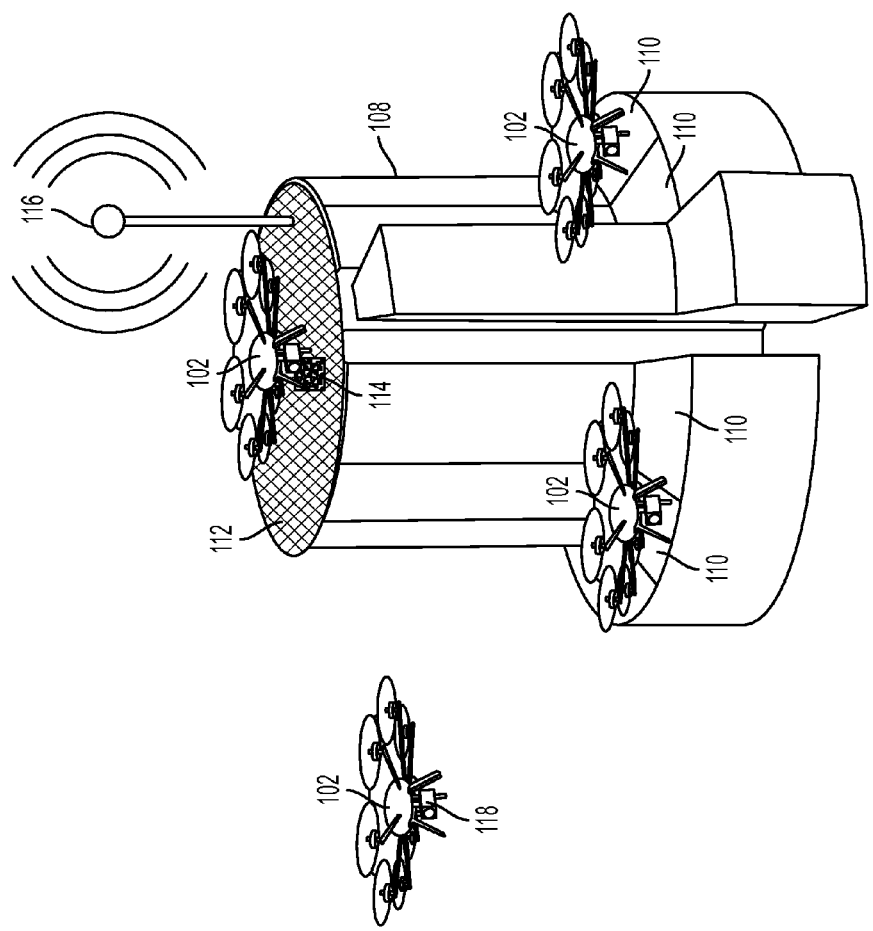
FIG. 2 illustrates a drone control facility according to a non-limiting embodiment.

Referring to FIG. 2, a drone control facility 108 is illustrated according to a non-limiting embodiment. The drone control facility 108 is configured to store or dock one or more drones 102 included in the drone-based microbial analysis sampling system 100. The electronic drone control facility 108 includes one or more charging stations 110 and a sampling station 112. The charging stations 110 are configured to electrically charge and/or re-energize a respective drone docked thereto. The charging station 110 can charge the drones 102 using, for example, wireless energized charging that charges an electronic rechargeable battery installed on a respective drone 102 as understood by one of ordinary skill in the art.

The sampling station 112 is configured to receive a specimen 114 from a respective drone 102 docked thereto. In response to receiving a specimen 114, the sampling station 112 can perform various microbial analysis operations and tests to determine whether the specimen tests positive for one or more microbials (i.e., microbes). The sampling station 112 may include various analysis and testing tools including, but not limited to, imaging analysis tools, a petri surface to cultivate microbes, and chemical applicators to apply chemicals to introduce chemicals and/or enzymes to the specimen that induce a chemical or other identifiable reaction when microbes are present. The drone control facility 108 can also be configured to automatically replace the sample collector device after the drone 102 delivers the specimen 114. For example, the drone can deliver a swab including a specimen 114 to the sampling station 112, and the drone control facility 108 can automatically replace the swab.

According to an embodiment, the drone control facility 108 can wirelessly communicate with one or more drones 102 via an antenna 116. In this manner, the drone control facility 108 can transmit various data including, but not limited to, location information indicating the location of a possible contaminated area 106. Similarly, the drone control facility 108 can also receive various data from one or more drones 102. For example, the drones 102 can transmit position data indicating a position of a respective drone 102 in the environment 104.

Figure 3:
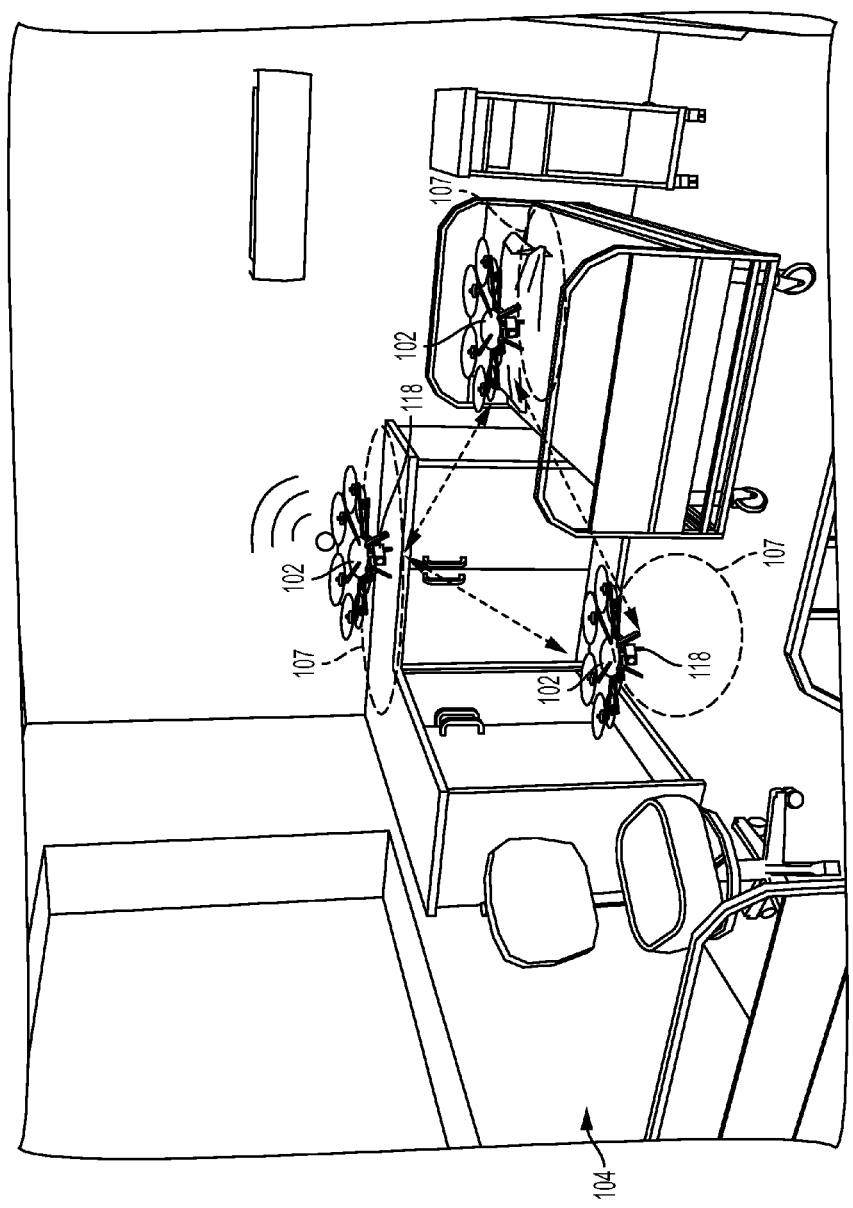
FIG. 3 illustrates an environment of a drone-based microbial sampling system including a plurality of sampling areas that include specimens collected by one or more drone vehicles according to a non-limiting embodiment.

Referring to FIG. 3, drones 102 are illustrated collecting specimens 114 from a medical facility (e.g., a hospital) environment 104. The medical facility environment 104 includes one or more areas of interest (AOI) 107 that may possibly contain one or more microbes. The AOI 107 can include a surface, wall, crevice, air sample, or accumulation of fluid. The AOI 107 can also be determined based on the surrounding environment. For example, AOIs 107 included in a warm, wet environment may be more susceptible to cultivation of certain microbes than cold, wet environments. Accordingly, certain AOIs 107 can be particularly sought out based on the surrounding environments. Various environmental conditions may include, but are not limited to, light conditions, temperature conditions, moisture, shape of surface, orientation of surface, and the material of the surface.

The drones 102 may include an onboard sampling unit 118 configured to sample a specimen 114 collected from an area of interest (AOI) 107. Specimen data can be collected in response to performing one or more microbial tests via the onboard sampling unit 118, and the specimen data can be delivered (e.g., wirelessly transmitted) from the drone 102 to the drone control facility 108. In response to receiving the specimen data, the drone control facility 108 can perform various microbial analysis operations or tests such as, for example, an imaging analysis, to determine whether the specimen 114 collected from the possible contaminated area 106 tests positive for one or more microbes. As discussed above, the drones 102 can also autonomously return to the drone control facility 108 and deliver the collected specimen such that microbial test can be performed.

Figure 4:
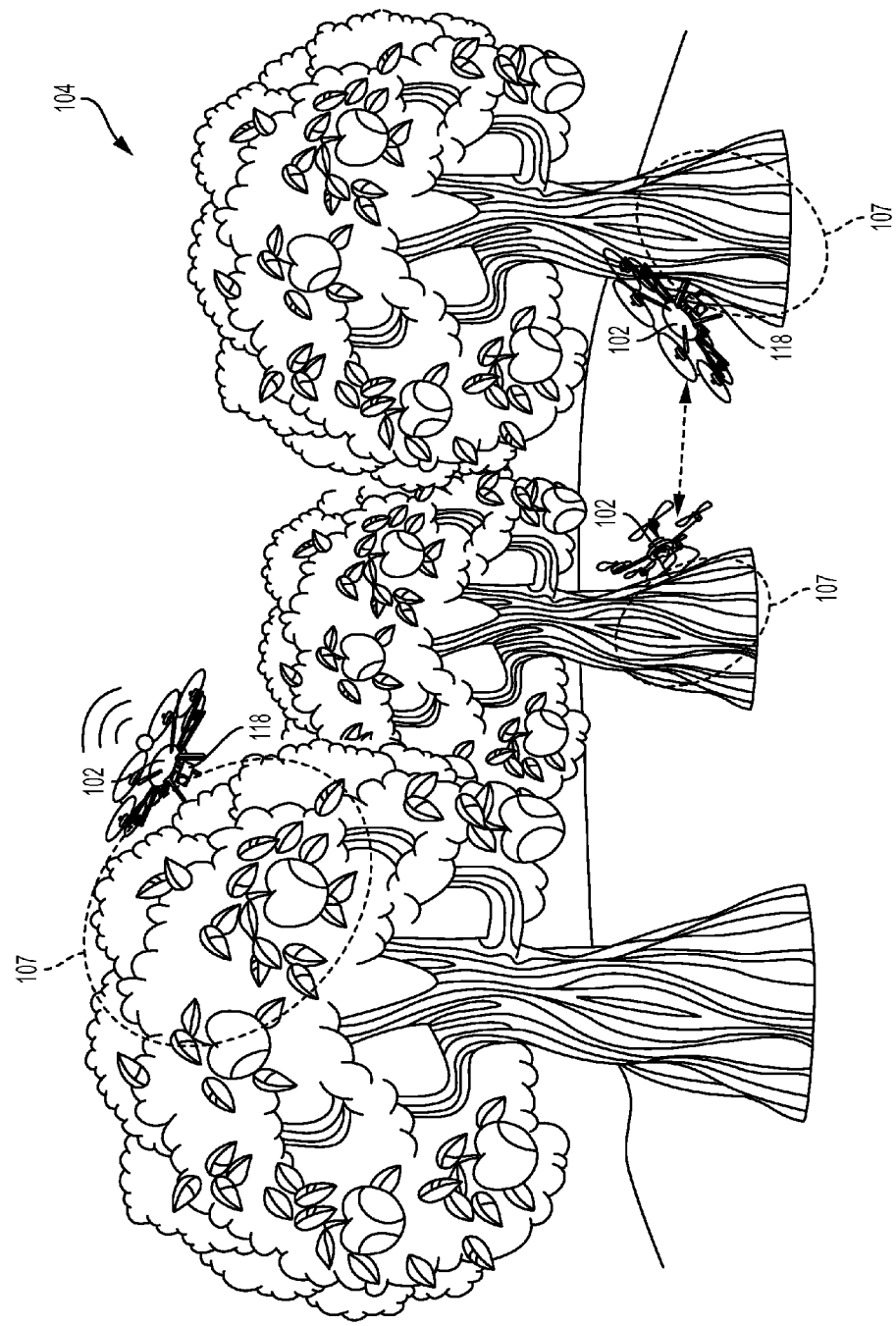
FIG. 4 illustrates an environment of a drone-based microbial sampling system including a plurality of sampling areas that include specimens collected by one or more drone vehicles according to another non-limiting embodiment.

Referring to FIG. 4, drones 102 are illustrated collecting specimens 114 from an agricultural acreage (e.g., a farm) environment 104. The agricultural acreage environment 104 includes one or more areas of interest (AOI) 107 that may possibly contain one or more microbes. In this case, for example, the AOI 107 includes, but is not limited to, leafs, bark, soil, air samples, and fluid samples. The AOI 107 can also be determined based on the surrounding environment. For example, AOIs 107 included in a warm, wet environment may be more susceptible to cultivation of certain microbes than cold, wet environments. Accordingly, certain AOIs 107 can be particularly sought out based on the surrounding environments. Various environmental conditions may include, but are not limited to, light conditions, temperature conditions, moisture, shape of surface, orientation of surface, and the material of the surface.

Similar to the features discussed above, the drones 102 may include an onboard sampling unit 118 configured to sample a specimen 114 collected from an area of interest (AOI) 107. Specimen data can be collected in response to performing one or more microbial tests via the onboard sampling unit 118, and the specimen data can be delivered (e.g., wirelessly transmitted) from the drone 102 to the drone control facility 108. In response to receiving the specimen data, the drone control facility 108 can perform various microbial analysis operations or tests such as, for example, an imaging analysis, to determine whether the specimen 114 collected from the possible contaminated area 106 tests positive for one or more microbes. As discussed above, the drones 102 can also autonomously return to the drone control facility 108 and deliver the collected specimen such that microbial test can be performed. The various microbial tests may include a statistical analysis that predicts the spread of microbes across the agricultural acreage environment 104.

Figure 5:
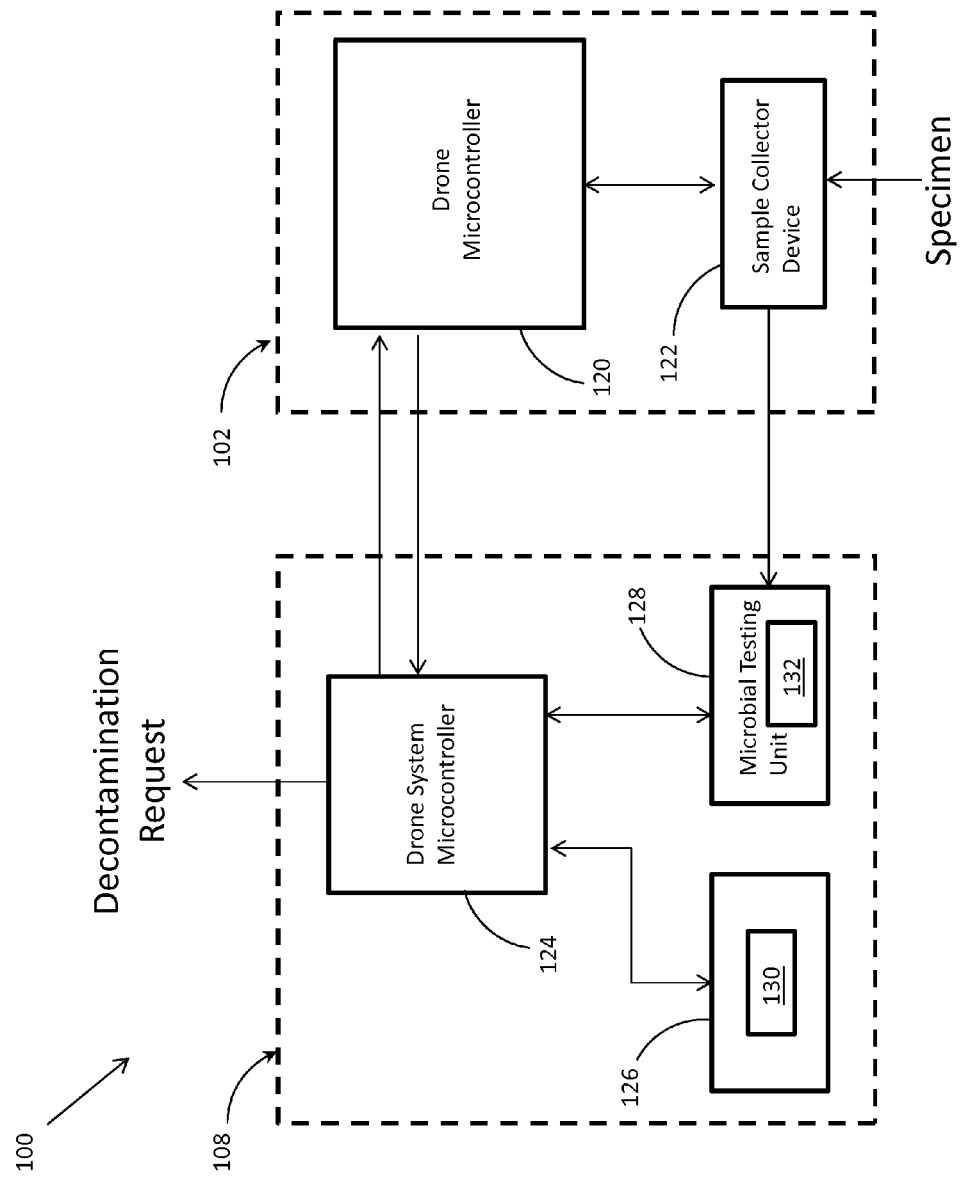
FIG. 5 is a block diagram illustrating a drone-based microbial sampling system according to a non-limiting embodiment.

Turning now to FIG. 5, a block diagram illustrating a drone-based microbial sampling system 100 is illustrated according to a non-limiting embodiment. The drone-based microbial sampling system 100 includes at least one drone vehicle 102 in signal communication with a drone control facility 108. The drone vehicle 102 includes a drone microcontroller 120 and a specimen collector device 122. The electronic drone microcontroller 120 is configured to autonomously operate and navigate the drone vehicle 102 as understood by one or ordinary skill in the art. In this manner, the drone vehicle 102 can autonomously navigate to one or more possible contaminated areas 106 indicated by the drone control facility 108. The specimen collection device 122 is configured to collect one or more specimens from a possible contaminated area 106. The sample collector device 122 may include, but is not limited to, a swab, a blade, and/or a container to store a collected specimen. Upon collecting one or more specimens, the drone vehicle 102 can autonomously return to the drone control facility 108 and automatically deliver the collected specimen as discussed in detail above.

The drone control facility 108 includes an electronic drone system microcontroller 124 in signal communication with an electronic microbial location database 126 and an electronic microbial testing unit 128. The microbial location database 126 stores a lookup table 130 (LUT) that is populated with at least one possible contaminated area previously determined to contain at least one positively tested microbe. In this manner, the drone system controller 124 can retrieve locations of one or more possible contaminated areas 106 from the LUT 130, transmit the location data retrieved from the LUT 130 to one or more drones 102, and command the drones 102 to navigate to the possible contaminated area 106 indicated by the location information. Although a description of sampling locations known to possibly contain microbes is discussed, it should be appreciated that the one or more drones 102 can be command to autonomously navigate about the environment 104 and perform samplings at one or more random locations.

The process of transmitting the location data and commanding the drones 102 to navigate toward the possible contaminated area 106 can be initiated in response to various conditions including, but not limited to, a microbial sampling request manually input to the drone control facility 108, a timed schedule that periodically requests a microbial sample analysis, detection of a specific-type of microbe, and/or detection of a microbial outbreak. A microbial outbreak may be detected, for example, when a number of positively tested contaminated areas exceeds a threshold value. It should be appreciated, however, that additional methods for determining a microbial outbreak may exist. In addition, when an outbreak is detected, the scheduling for initiating microbial samplings can be modified. For example, the frequency at which microbial samplings are preformed is increased during an outbreak, as compared to normal non-outbreak conditions.

The microbial testing unit 128 performs one or more microbial tests on a specimen delivered from a drone 102. As discussed above, the microbial tests may include, but are not limited to, imaging analysis tools, a petri surface to cultivate microbes, and chemical applicators to apply chemicals to introduce chemicals and/or enzymes to the specimen that induce a chemical or other identifiable reaction when microbes are present. Based on the testing results, the microbial testing unit 128 determines whether the specimen obtained from the possible contaminated area 106 tests positive for one or more microbes. For example, the microbial testing unit 128 may extract images from the specimen from the drone and compare the extracted images to one or more predetermined images of microbes that are stored in a microbe information database 132 included in the microbial testing unit 128. When an extracted image matches a stored image from the microbe information database 132, the microbial testing unit 128 determines that the possible contaminated area 106 tests positive for microbes matching the stored microbial image. The aforementioned image matching technique is but one method of determining that the possible contaminated area 106 tests positive for microbes and it should be appreciated that other methods for testing the specimen can be used.

Based on the microbial testing results, the drone system microcontroller 124 can update the LUT 130. For example, if the microbial testing results indicate that the specimen tests negative for microbes (i.e., does not contain microbes), the drone system microcontroller 124 can update the LUT 130 indicating that the possible contaminated area 106 does not contain microbes at a particular time and/or date. According to an embodiment, after a number of negative tests exceeds a threshold value, the drone system microcontroller 124 can determine that the possible contaminated area 106 is not likely to include microbes and can remove the location of the possible contaminated area 106 from the LUT 130.

When, however, the specimen tests positive for microbes (i.e., the specimen contains microbes), the drone system microcontroller 124 can update the LUT 130 and indicate that the possible contaminated area 106 from which the specimen was collected contains microbes. For instance, the LUT 130 can be updated with the particular types of microbes existing in the contaminated area 106 and the date/time at which the microbes were detected. In addition, the drone system microcontroller 124 can prioritize a plurality of possible contaminated areas in the LUT 130 based on the number of positive test results. For example, locations that frequently test positive for microbes can be prioritized higher. In this manner, the drone control facility 108 can monitor higher priority areas more frequently than lower priority areas.

According to a non-limiting embodiment, the drone system microcontroller 124 can further output an electronic service request in response to receiving an electrical signal from the microbial testing unit 128 indicating that the possible contaminated area 106 tested positive for microbes. A service request may include, for example, an alert or a service request signal, to request decontamination of the positively contaminated area. The decontamination may include, but is not limited to, dispatching a cleaning crew to wipe down and disinfect the positively contaminated area and/or dispatching one or more decontamination drones to the positively contaminated area. The decontamination drones may seek out and identify areas that correspond to the specimen and can disinfect the contaminated areas using various methods including, but not limited to, spraying disinfectant and/or exposing the contaminated area to ultraviolet (UV) light or other types of energy known to kill microbes. According to an embodiment, the decontamination drones 102 can be commanded to swarm to an area that tests positive for one or microbes with the intention to more efficiently contain the spread of microbes. The command to swarm the drones 102 includes commanding the drones 102 to congregate, hover, or occur in groups or multitudes at a positively tested area. It should be appreciated that the decontamination drones may include drones 102 included that perform the initial specimen collection and/or drones that did not perform the specimen collection.

Figure 6:
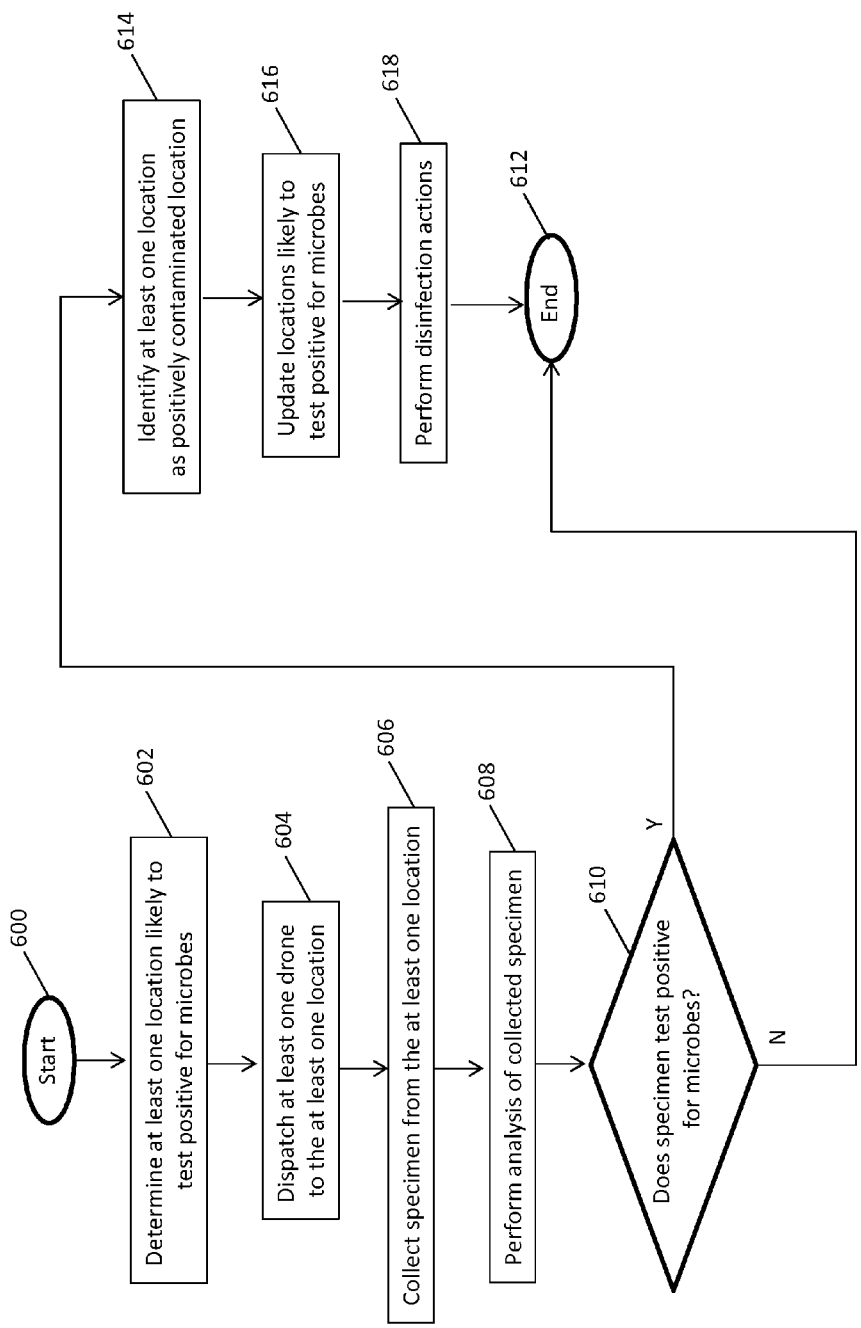
FIG. 6 is a flow diagram illustrating a method of performing a microbial sampling analysis according to a non-limiting embodiment

Referring now to FIG. 6, a flow diagram illustrates a method for performing a microbial analysis according to a non-limiting embodiment. The method begins at operation 600, and determines at least one location likely to test positive for microbes at operation 602. At operation 604, at least one drone is dispatched to the at least one location, and one or more specimens are collected from the at least one location at operation 606. At operation 608, an analysis including one or more microbial tests are performed on specimen data collected from the at least one location. The specimen data can include the specimen itself collected by the drone and/or specimen data generated by the drone and transmitted to an electronic microbial testing unit.

Turing to operation 610, a determination is made as to whether the specimen tests positive for microbes. If the specimen does not test positive for microbes, i.e., the specimen does not contain microbes, the method ends at operation 612. If, however, the specimen does test positive for microbes at operation 610, the at least one location is identified as a positively contaminated location at operation 614. At operation 616, locations likely to test positive for microbes are updated. For instance, a lookup table (LUT) containing one or more locations likely to test positive for microbes is updated by indicating that a location included in the LUT does indeed test positive for microbes, or a new location is added to a LUT indicating that the new location tests positive for microbes. At operation 618, one or more disinfection actions are performed in order to exterminate the microbes from the positively contaminated location, and the method ends at operation 612.

A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

As used herein, the term module refers to a hardware module including an Application Specific Integrated Circuit (ASIC), an electronic circuit, a computer processor (shared, dedicated, or group) and memory that store one or more executable software or firmware programs, a combinational logic circuit, and/or other suitable components that provide the described functionality.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the inventive teachings and the practical application, and to enable others of ordinary skill in the art to understand the invention for various embodiments with various modifications as are suited to the particular use contemplated.

The flow diagrams depicted herein are just one example. There may be many variations to this diagram or the operations described therein without departing from the spirit of the invention. For instance, the operations may be performed in a differing order or operations may be added, deleted or modified. All of these variations are considered a part of the claimed invention.

While various embodiments have been described, it will be understood that those skilled in the art, both now and in the future, may make various modifications which fall within the scope of the claims which follow. These claims should be construed to maintain the proper protection for the invention first described.

What is claimed is:

1. A method of performing a microbial analysis, the method comprising:
    determining at least one possible contaminated area;
    autonomously navigating at least one drone vehicle to the at least one possible contaminated area to collect at least one specimen;
    performing a microbial analysis based on the collected at least one specimen; and
    confirming the at least one possible contaminated area is a positively contaminated area that contains at least one microbe based on the microbial analysis.

2. The method of claim 1, further comprising performing at least one decontamination operation to decontaminate the positively contaminated area in response to determining that the at least one possible contaminated area tests positive.

3. The method of claim 1, further comprising transmitting location data indicating the at least one possible contaminated area to the at least one drone vehicle such that the drone vehicle autonomously navigates to the at least one possible contaminated area.

4. The method of claim 3, wherein the at least one drone vehicle autonomously returns to the electronic drone control facility in response to collecting at least one specimen to deliver the collected at least one specimen.

5. The method of claim 4, further comprising performing the microbial analysis on the at least one specimen delivered by the at least one drone vehicle.

6. The method of claim 5, further comprising transmitting specimen data to the electronic drone control facility.

7. The method of claim 6, further comprising performing the microbial analysis based on at least one of the delivered specimens and the transmitted specimen data.

8. The method of claim 1, further comprising generating a lookup table (LUT) populated with the at least one possible contaminated area previously determined to contain at least one positively-tested microbe and updating the LUT in based on a result of the microbial analysis.

* * * * *